United States Patent [19]

Green et al.

[11] Patent Number: 4,893,622
[45] Date of Patent: Jan. 16, 1990

[54] METHOD OF STAPLING TUBULAR BODY ORGANS

[75] Inventors: David T. Green, Norwalk; Herbert W. Korthoff, Wilton, both of Conn.

[73] Assignee: United States Surgical Corporation, Norwalk, Conn.

[21] Appl. No.: 176,229

[22] Filed: Mar. 31, 1988

Related U.S. Application Data

[62] Division of Ser. No. 920,581, Oct. 17, 1986, Pat. No. 4,752,024.

[51] Int. Cl.[4] .............................................. A61B 17/04
[52] U.S. Cl. .................................................... 227/180
[58] Field of Search ........................ 128/334 R, 334 C; 227/19, DIG. 1

[56] References Cited

U.S. PATENT DOCUMENTS

| | | | |
|---|---|---|---|
| 3,193,165 | 7/1965 | Akhalaya | 227/DIG. 1 |
| 4,319,576 | 3/1982 | Rothfuss | 128/334 R |
| 4,423,730 | 1/1984 | Gabbay | 128/334 R |
| 4,476,863 | 10/1984 | Kanshin et al. | 128/334 R |
| 4,505,272 | 3/1985 | Ufyamyshev et al. | 128/334 R |
| 4,505,414 | 3/1985 | Filipi | 227/19 |
| 4,592,354 | 6/1986 | Rothfuss | 128/305 |
| 4,703,887 | 11/1987 | Clanton et al. | 128/334 R |

Primary Examiner—Edward M. Coven
Assistant Examiner—Gary Jackson
Attorney, Agent, or Firm—Kenyon & Kenyon

[57] ABSTRACT

The two-part surgical fastener is composed of an annular stapling part having projecting prongs and an annular retaining part having an annular gap which receives the prongs. The anvil assembly on which the retaining part of the fastener is mounted has fingers which can be collapsed radially inwardly after stapling to permit ease of removal. During stapling, the annular stapling part is driven through the tubular ends of the tissue into retained engagement with the retaining part. At the same time, the clamped ends of the tissue are cut on a circular line and, thereafter, the anvil assembly is collapsed radially inwardly to permit withdrawing of the stapling apparatus.

4 Claims, 13 Drawing Sheets

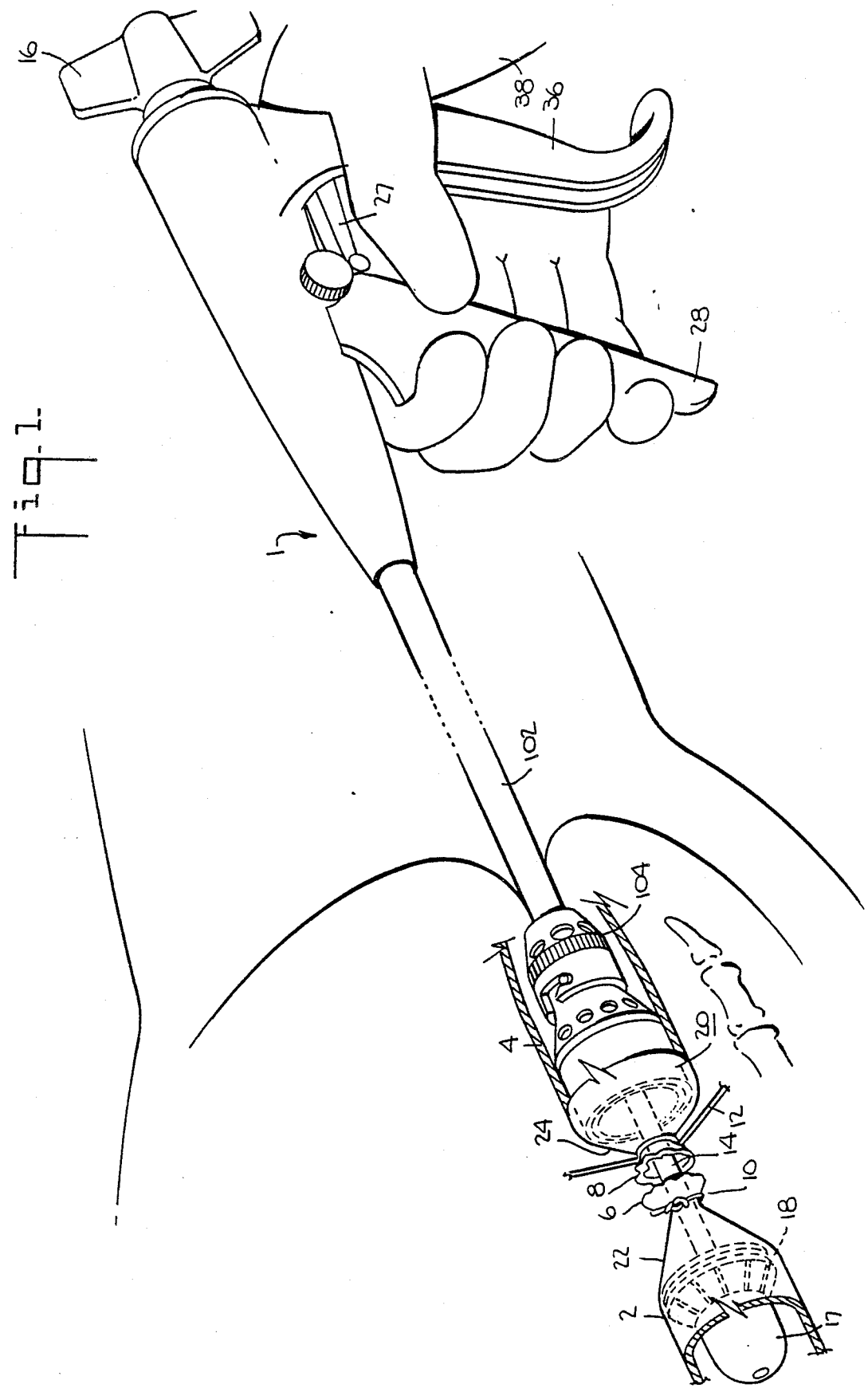

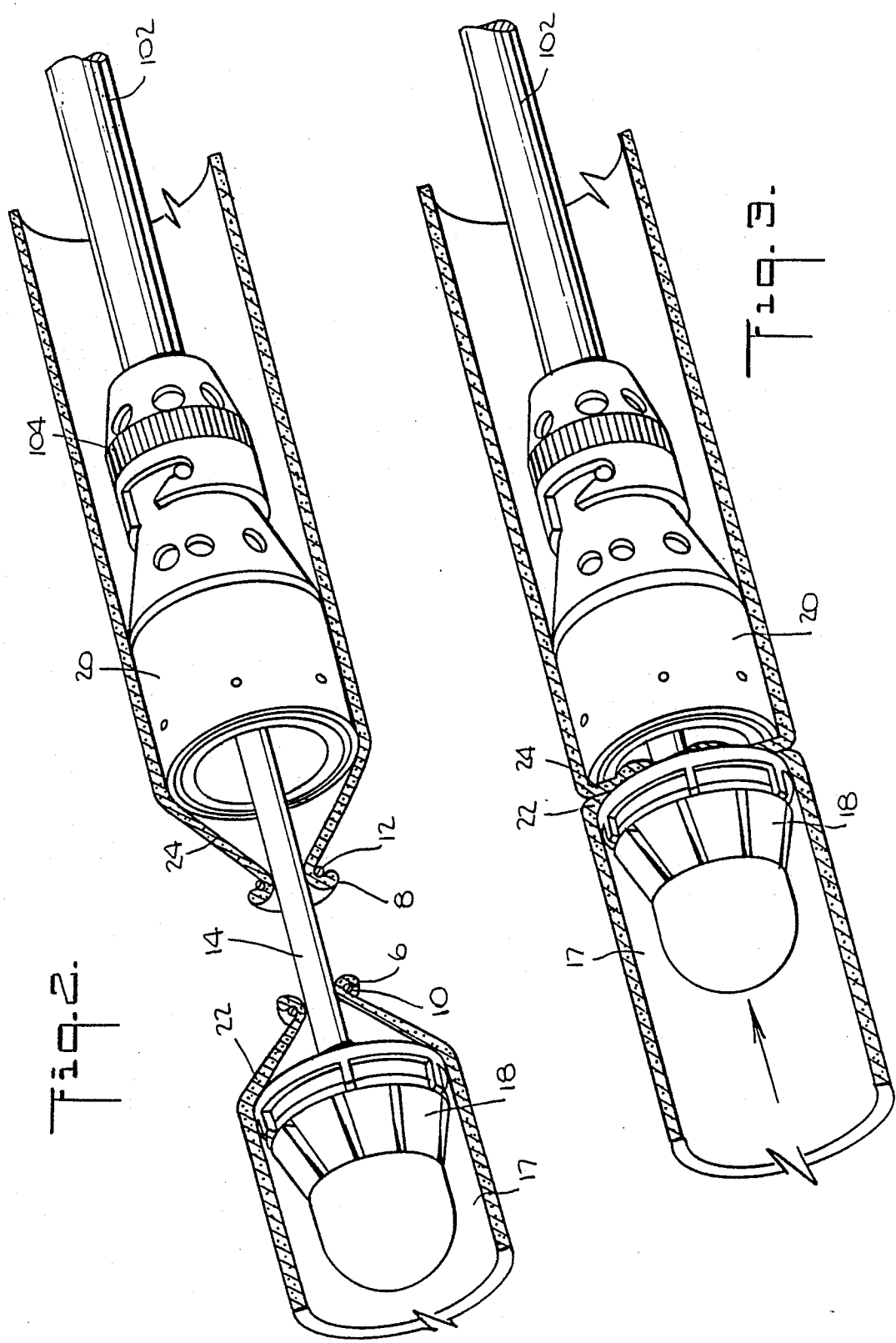

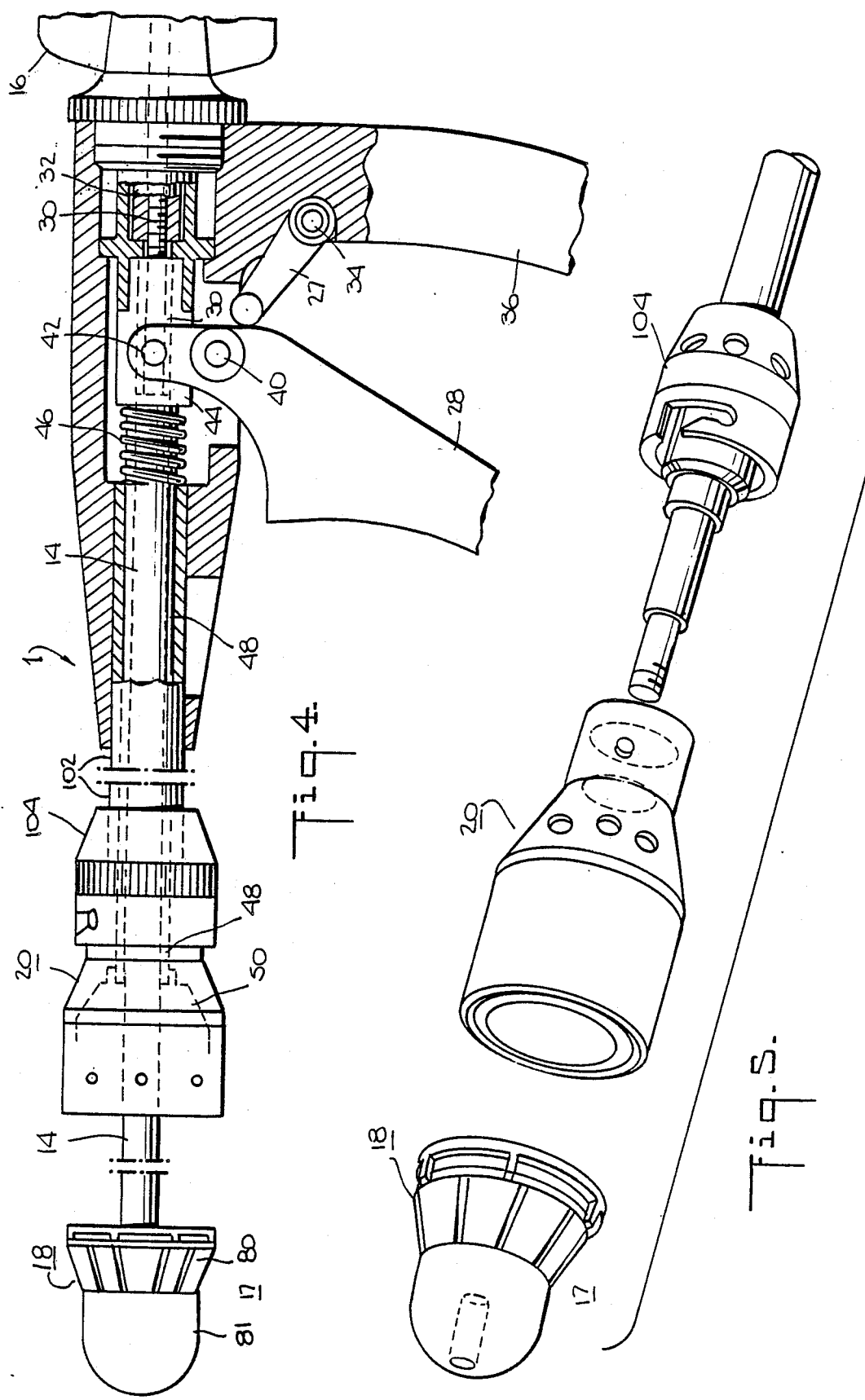

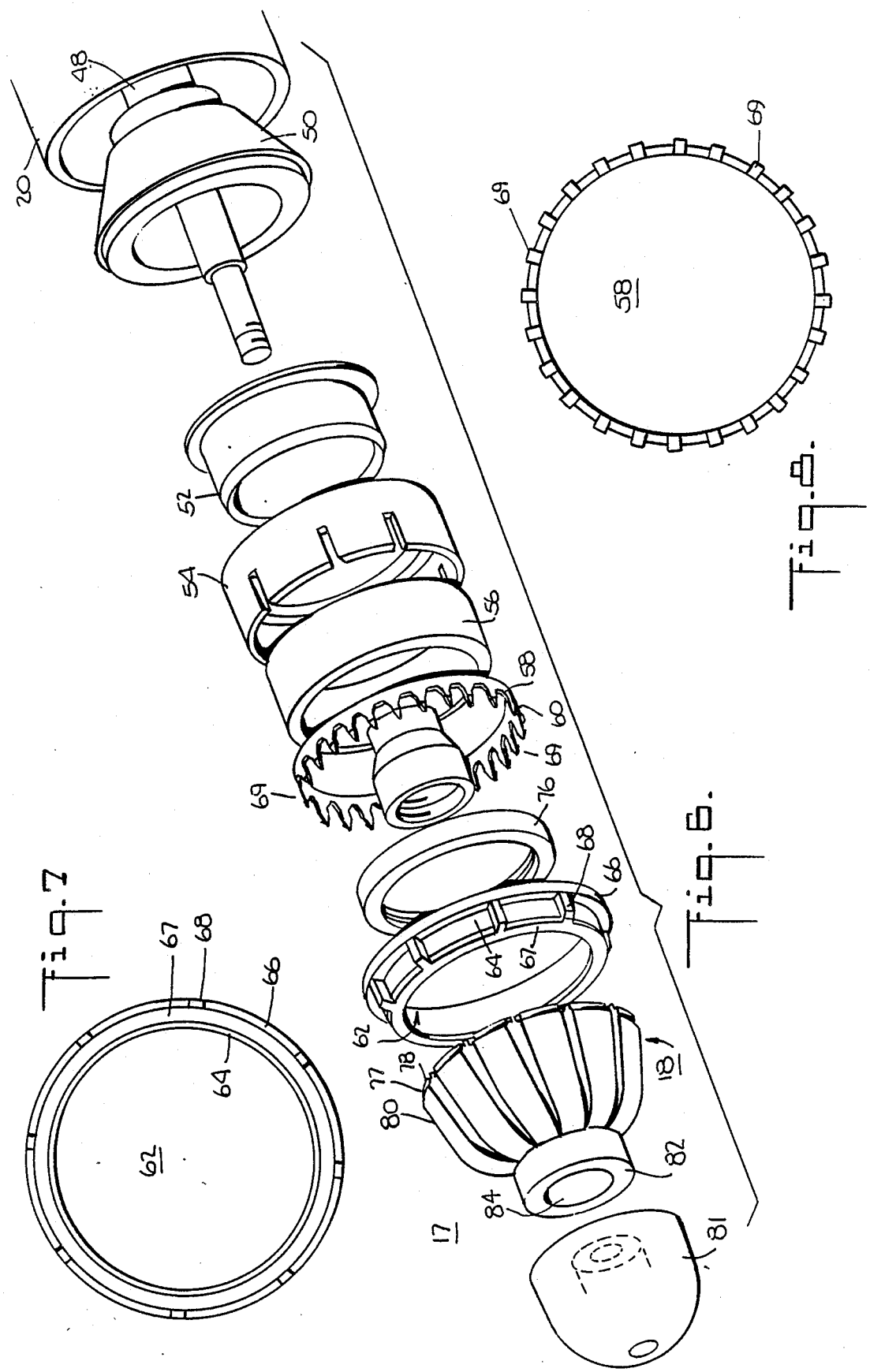

METHOD OF STAPLING TUBULAR BODY ORGANS

This is a division of application Ser. No. 920,581, filed Oct. 17, 1986, now U.S. Pat. No. 4,752,024.

This invention relates to a method of stapling tubular body organs.

Heretofore, various types of surgical stapling devices have been known wherein a stapling function takes place at a location which is relatively remote from the location at which the stapling device is held and actuated by an operator. For example linear closure surgical stapler devices are described in U.S. Pat. No. 3,494,533 and circular anastomosis surgical stapler devices are described in U.S. Pat. Nos. 4,304,236; 4,351,466; 4,473,077 and 4,488,523 as well as U.S. Pat. Nos. 273,041 and 271,944. Typically, the stapling devices described in these patents operate by placing tissue to be stapled in a clamped manner between an anvil assembly and a fastener holding assembly, both of which are located at the distal end of the instrument. The clamped tissue is stapled by driving one or more fasteners from the holding assembly so that the ends of the fasteners pass through the tissue and are formed properly by contact with the anvil assembly. The forces required to operate the instrument are applied by the operator of the instrument to one or more actuator elements located at or near the proximal end of the instrument. The distal and proximal portions of the instrument are joined by a longitudinal connecting shaft struccture along which the actuating forces and motions are transmitted to the distal operation elements. This type of construction, including relatively widely spaced distal and proximal portions, may be employed for any of several reasons, such as the relative inaccessibility of the tissue to be stapled, the need for good visibility of the tissue during stapling, and the like.

These known types of surgical stapler devices generally use a plurality of small and discrete fasteners requiring precise registration with the anvil assembly to ensure that proper fastener formation occurs during the stapling operation.

It is an object of the invention to eliminate the need for a plurality of precisely registered small and discrete fasteners in anastomosis stapling devices.

It is another object of the invention to easily and quickly install a surgical stapler in tissue.

It is another object of the invention to eliminate the need for a high degree of rotational accuracy in the registration of a fastener holder relative to an anvil assembly in an anastomosis stapling device.

The invention provides a method of stapling the tubular ends of a pair of vessels together which includes the steps of clamping the tubular ends of the vessels between an anvil assembly and a surgical fastener holding assembly, driving an annular stapling part through the clamped ends of the tissue into an annular retaining part removably supported on the anvil assembly and severing the clamped ends on a circular cutting line disposed radially within the stapling part. In addition, the method includes the steps of moving the anvil assembly away from the stapled ends of the tissue to withdraw the anvil assembly from the annular retaining part, thereafter, collapsing the anvil assembly radially inwardly of the retaining part and the cutting line and then withdrawing the stapling apparatus from the stapled-together vessels.

These and other objects and advantages of the invention will become more apparent from the following detailed description taken in conjunction with the accompanying drawings wherein:

FIG. 1 illustrates a perspective view of a surgical stapling apparatus constructed in accordance with the invention in place within an intestine;

FIG. 2 illustrates a perspective view of the distal end of the stapling apparatus prior to fastening;

FIG. 3 illustrates a view similar to FIG. 2 of the distal end of the stapling apparatus during a stapling operation;

FIG. 4 illustrates a part sectional side view of the apparatus of FIG. 1;

FIG. 5 illustrates an exploded view of the distal end of the apparatus of FIG. 1;

FIG. 6 illustrates an exploded view of a surgical fastener, anvil assembly and holding assembly in accordance with the invention;

FIG. 7 illustrates a front view of an annular retaining part in accordance with the invention;

FIG. 8 illustrates a front view of an annular stapling part in accordance with the invention;

Figure 9:
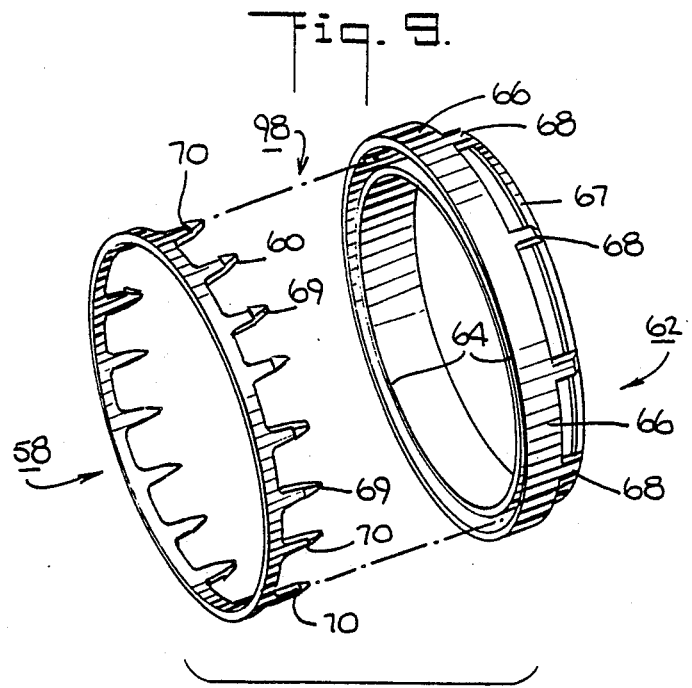
FIG. 9 illustrates an exploded view of the retaining part and stapling part in accordance with the invention.

Referring to FIGS. 1 and 4, the surgical stapling apparatus 1 is used, for example for the stapling of two ends 2, 4 of an intestine wherein a section of the intestine has been surgically removed between cut ends 6, 8. As indicated in FIG. 1, the cut ends 6, 8 of the intestine are generally tied with suture material 10, 12 with conventional purse-string suturing being used.

The stapling apparatus 1 includes a shaft 14 and a hand screw 16 which is articulated to the shaft 14 in order to move the shaft 14. As indicated in FIG. 4, the apparatus 1 includes an anvil assembly 17 which is mounted on a distal end of the shaft 14 and includes an anvil 18 which faces a surgical fastener holding assembly 20 which is also mounted on the shaft 14 for relative movement with the anvil assembly 17 to maintain the two ends of the intestine areas 22, 24 therebetween.

Referring to FIG. 4, the shaft 14 is provided with a screwthread 30 at the proximal end which mates in an internally threaded sleeve extension 32 of the hand screw 16. The sleeve extension 32 is secured to the hand screw 16 so that both turn together and thus the rotation of the hand screw 16 causes longitudinal movement of the shaft 14. By tightening the hand screw 16, the anvil assembly can be moved towards the holding assembly 20 so that the tissue can be clamped therebetween with proper spacing between the anvil assembly 17 and the holding assembly 20. Calibration means (not shown) may be provided to ensure proper spacing, for example as described in U.S. Pat. No. 4,473,077.

The apparatus 1 is also provided with a handle 36 and a trigger 28 which is pivotally mounted on a pivot pin 40 secured in the housing of the apparatus 1. A safety latch 27 is also pivotally mounted on a pivot pin 34 on the handle 36 in order to prevent pivoting of the trigger 28. In addition, the trigger 28 is articulated in known manner, for example via a pusher 42 to a slider 44 disposed about the shaft 14. This slider 44 abuts a compression spring 46 in order to apply a biasing force on a tube 48 concentric of the sleeve 14 in order to move the tube 48 distally upon actuation of the trigger 28. The tube 48, in turn, cooperates with an actuator 50 in order to perform a stapling operation.

Referring to FIGS. 4 and 5, the shaft 14 has a threaded distal end on which the anvil assembly 17 is mounted in threaded manner. In addition, a bayonet mount 104 is secured, in known manner on the tube 48. In this regard, the holding assembly 20 includes a sleeve at the proximal end which carries a pin for fitting into the bayonet connection of the mount 104. As indicated in FIG. 4, a sheath 102 is provided over the central part of the instrument and has a tubular portion 53 fitting within the bayonet mount 104 (see FIG. 12).

Referring to FIGS. 2 and 3, when the apparatus is initially put in place, the cut ends 6, 8 of the body tissue are drawn in about the shaft 14 with the anvil assembly 17 in a spaced condition relative to the holding assembly 20. During stapling, the anvil assembly 17 is drawn against the holding assembly 20 so as to clamp the ends of the tissue between the anvil assembly 17 and the holding assembly 20 (see FIG. 3).

Figure 12:
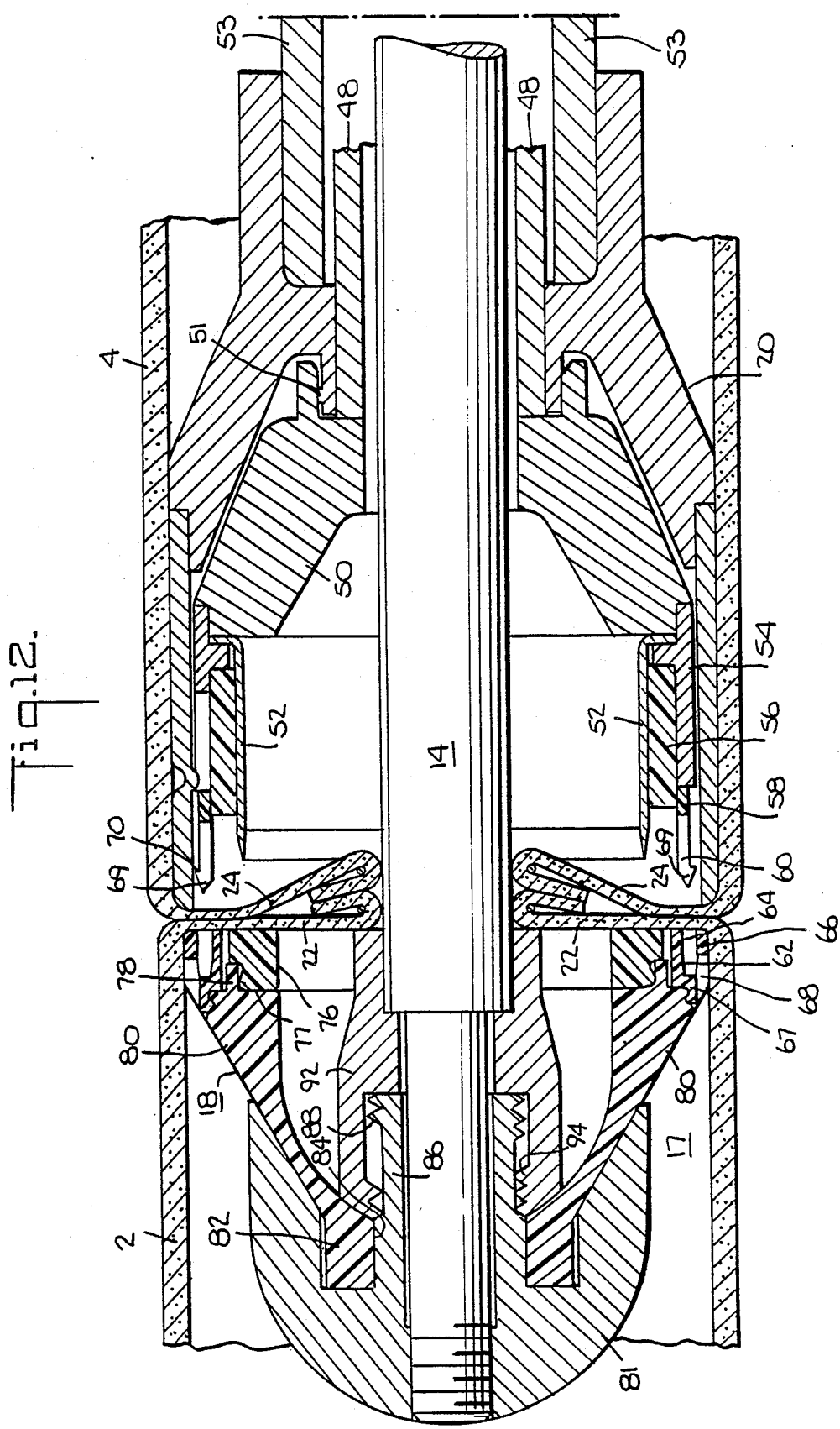
FIG. 12 illustrates a cross sectional view of the stapling components of the apparatus during an initial phase of stapling.

Referring to FIGS. 6 and 12, the actuator means includes an actuator 50 which is abutted against the distal end of the tube 48 and is disposed within the holding assembly 20. In this respect, the holding assembly is provided with a pad 51 which frictionally retains the actuator 50 in place until the actuator 50 is driven clear of the pad 51 by the tube 48. The actuator 50 carries an annular push ring 54 as well as an annular blade or scalpel 52 which is retained between the actuator 50 and push ring 54. In addition, a plastic spacer ring 56 is concentrically disposed between the push ring 54 and the annular scalpel 52. As indicated in FIG. 6, the push ring 54 is provided with a plurality of circumferentially disposed slots at the distal end.

An annular stapling part 58 is mounted about the spacer ring 56 and against the push ring 54 (see FIG. 12) and has a plurality of axially extending circumferentially spaced prongs 60.

The anvil 18 is made of resilient material and has a plurality of radiating fingers 80 extending angularly outwardly from a central hub 82 concentrically disposed about the longitudinal axis of the shaft 14. In this regard, the anvil 18 is made of one piece with several fingers 80. As indicated in FIG. 6, the anvil 18 has a somewhat frustum-like shape with the cylindrical hub 82 at the distal end. In addition, each finger 80 tapers in both thickness and width from the free end to the hub 82. In addition, the free end of each finger 80 has an extension 78 which forms a basal ridge as well as an annular reaction surface 77 within the extension 78.

An annular cutting block 76 is removably mounted within the outer ends of the fingers 80. That is, the cutting block 76 abuts against the reaction surfaces 77 of the fingers 80 within the extension 78. As indicated in FIG. 12, the cutting block 76 is aligned with the annular scalpel 52 and is made of a material so as to be penetrated by the cutting edge of the scalpel 52. The cutting block 76 is also shaped so as to be fitting into and about the extensions 78 in a slide fit manner.

An annular retaining part 62 is also mounted at the free ends of the fingers 80 of the anvil 18. As indicated, the retaining part 62 includes an inner cylindrical guide wall 64 and an outer retaining ring 66 which are concentrically disposed relative to each other to define an annulgar gap for receiving the prongs 60. Suitable means in the form of posts 68 (FIG. 8) are provided to secure the retaining rings 66 to the cylindrical wall 64. An annular flange 67 is also provided between the post 68 and the guide wall 64 (FIG. 7).

Figure 10:
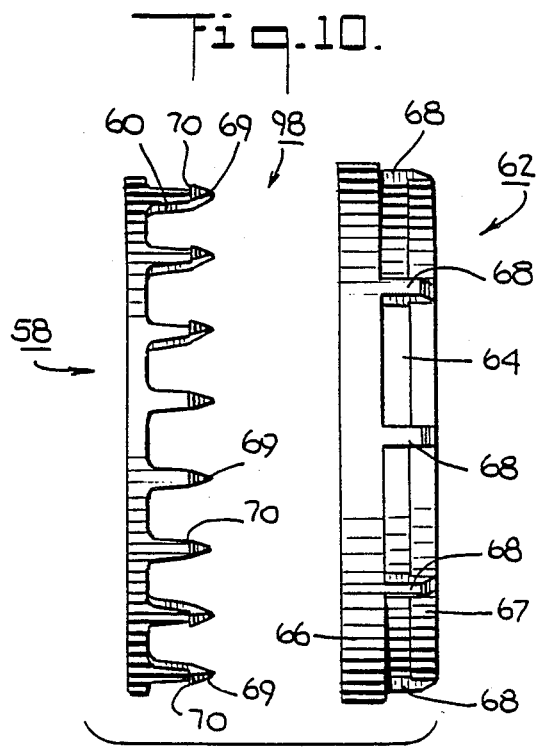
FIG. 10 illustrates side views of the retaining part and stapling part of FIG. 9.

Referring to FIGS. 9 and 10, wherein like reference characters indicate like parts as above, each prong 60 of the stapling part 58 has a sharp tip for piercing tissue while the retaining part 62 is positioned to receive the prongs 60. Catch means are also provided for holding the prongs 60 in the retaining part 62 in order to clamp the pierced tissue therebetween. As illustrated, the catch means includes a radially extending barb 69 on each prong 60 with a proximally facing surface 70 which can be engaged against the retaining ring 66 of the retaining part 62. As indicated, each barb 69 extends radially outwardly of a prong 60 so that the proximally facing surface 70 can be engaged against the retaining ring 66.

The annular stapling part 58 and annular retaining part 62 form a surgical fastening 98 which is of relatively simple construction. Both parts 58, 62 can be rotated relative to the other and need not be precisely registered in order to provide for stapling.

When the two parts 58, 62 are brought togehter, the prongs 60 pierce the tissue and then enter into the gap between the guide walls 64 and retaining ring 56. At this time, the guide walls 64 and rings 66 temporarily deform due to the wedging action of the barbs 69. After the barbs 69 clear the retaining ring 66, the ring 66 and wall 62 snap back into their normal relationship in which the surfaces 70 of the barbs 69 engage against the retaining ring 66 thus securing the parts 58, 62 together while also clamping the two ends of tissue together. Of note, the flange 67 protects uninvolved tissue from the sharp ends of the prongs 60 (see FIG. 13).

Referring to FIGS. 6 and 12, the anvil assembly 17 also includes an anvil head 81 having an internal conical wall which receives the anvil with the fingers 80 abutting against the wall. In addition, the anvil head 81 has a central shaft 86 about which the hub 82 is mounted via an axial opening 84. The shaft 86 also has an external screw thread 88 on which a hub retainer 92 is threaded via internal screw threads 94. The hub retainer 92 is thus able to freewheel in relation to the anvil head 81, that is, the hub retainer 92 can be threaded into abuttment with the hub 82 with a greater or lesser degree of force. In this way, the anvil head 81 and retainer 92 cooperate to form a means for biasing the fingers 80 of the anvil 18 radially inwardly of the cutting block 76 to permit movement of the fingers 80 radially inwardly in response to removal of the cutting block 76 from the fingers 80. As indicated in FIG. 12, cutting block 76 holds the fingers 80 in a tensioned state. In addition, the fingers 80 are suitably shaped so as to hold the retaining part 62 in a snap fit relation (see FIG. 12). When the cutting block 76 and retaining part 62 are in place, dimensional stability is imparted to the resilient fingers 80.

As indicated in FIG. 12, while the anvil 18 is made of a plastic, the anvil head 81 and retainer ring 92 are made of a metal, such as aluminum. Further, the anvil head 81 is provided with a threaded bore so as to be threaded onto the distal end of the central shaft 14.

Figure 11:
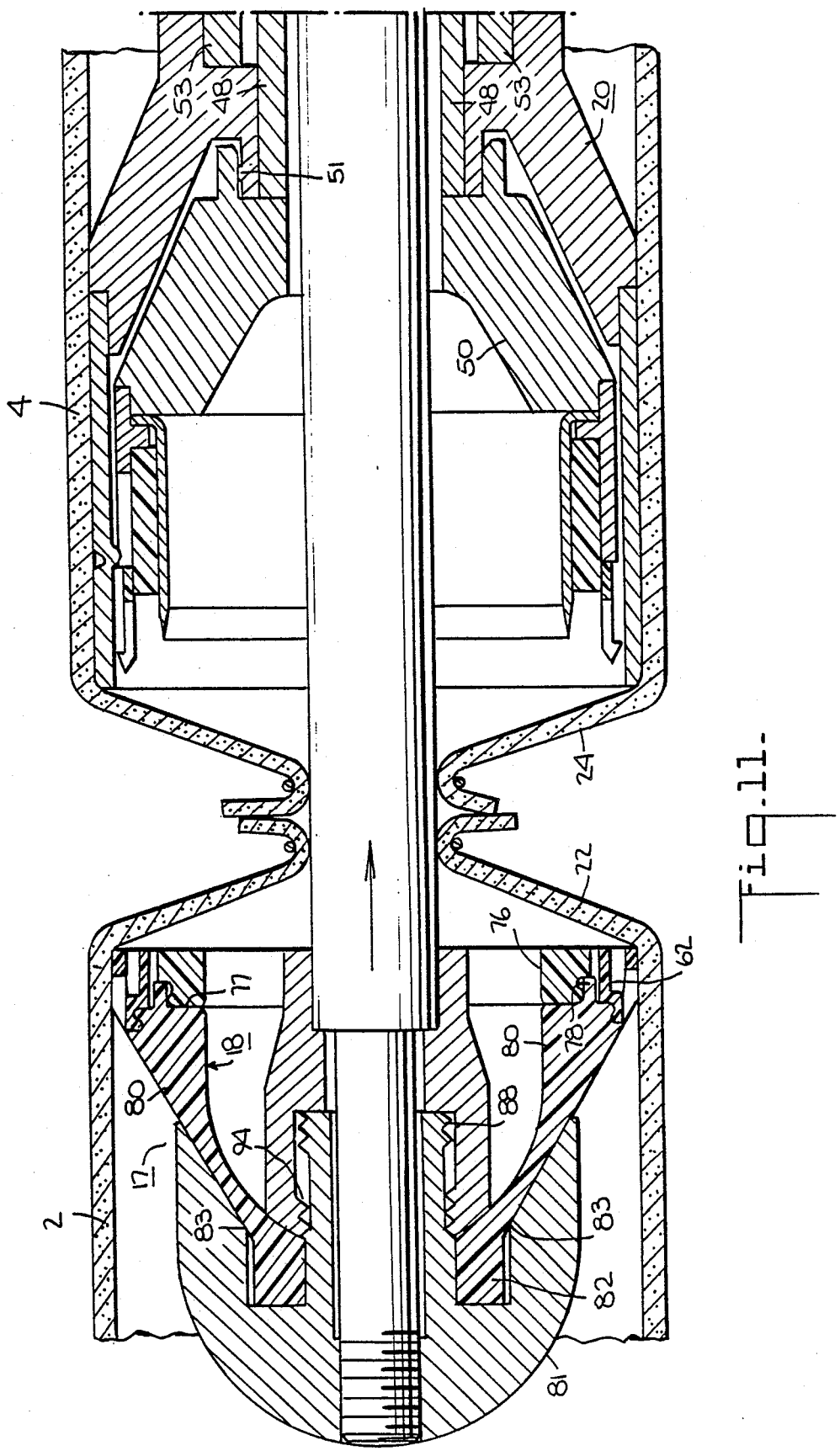
FIG. 11 illustrates a view of the distal end of the surgical stapling apparatus prior to stapling.
Figure 13:
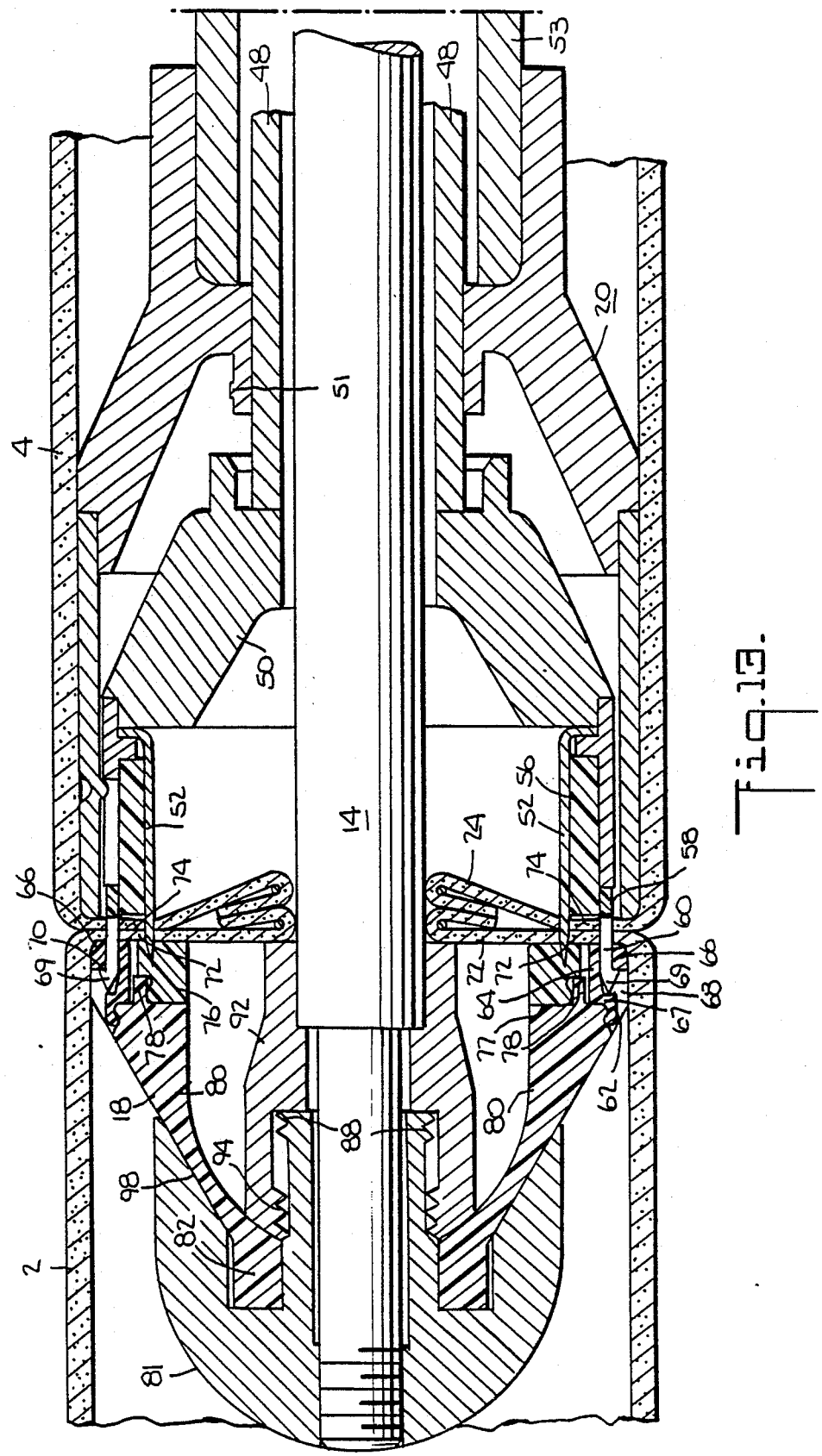
FIG. 13 illustrates a view similar to FIG. 12 of the stapling components after stapling.

Referring to FIG. 11, in use, in order to staple the tubular ends of the tissue together, the stapling apparatus is inserted in a conventional manner. Thereafter, the ends of the tissue 2, 4 are pulled together as indicated in FIG. 11 about the central shaft 14 so as to dispose two areas 22, 24 between the anvil assembly 17 and the fastener holding assembly 20. Thereafter, the shank 14 is moved proximally via the hand screw 16 so as to move the anvil assembly 17 into a clamped position with the holding assembly 20. In this position, the areas 22, 24 of the tissue 2, 4 are clamped between the anvil 18 and the holding assembly 20. Next, triggering of the instrument via the trigger 28 (see FIG. 1) causes the tube 48 to be moved distally. This in turn moves the actuator 50 distally. As a result, the annular scalpel 52 severs the clamped ends of the tissue on a circular cutting line 99 while penetrating into the cutting block 76. At the same time, the push ring 54 pushes the prong 60 of the stapling part 58 through the clamped ends of the tissue into the annular retaining part 62 with the barb 69 engaging behind the retaining ring 66 as indicated in FIG. 13.

Figure 14:
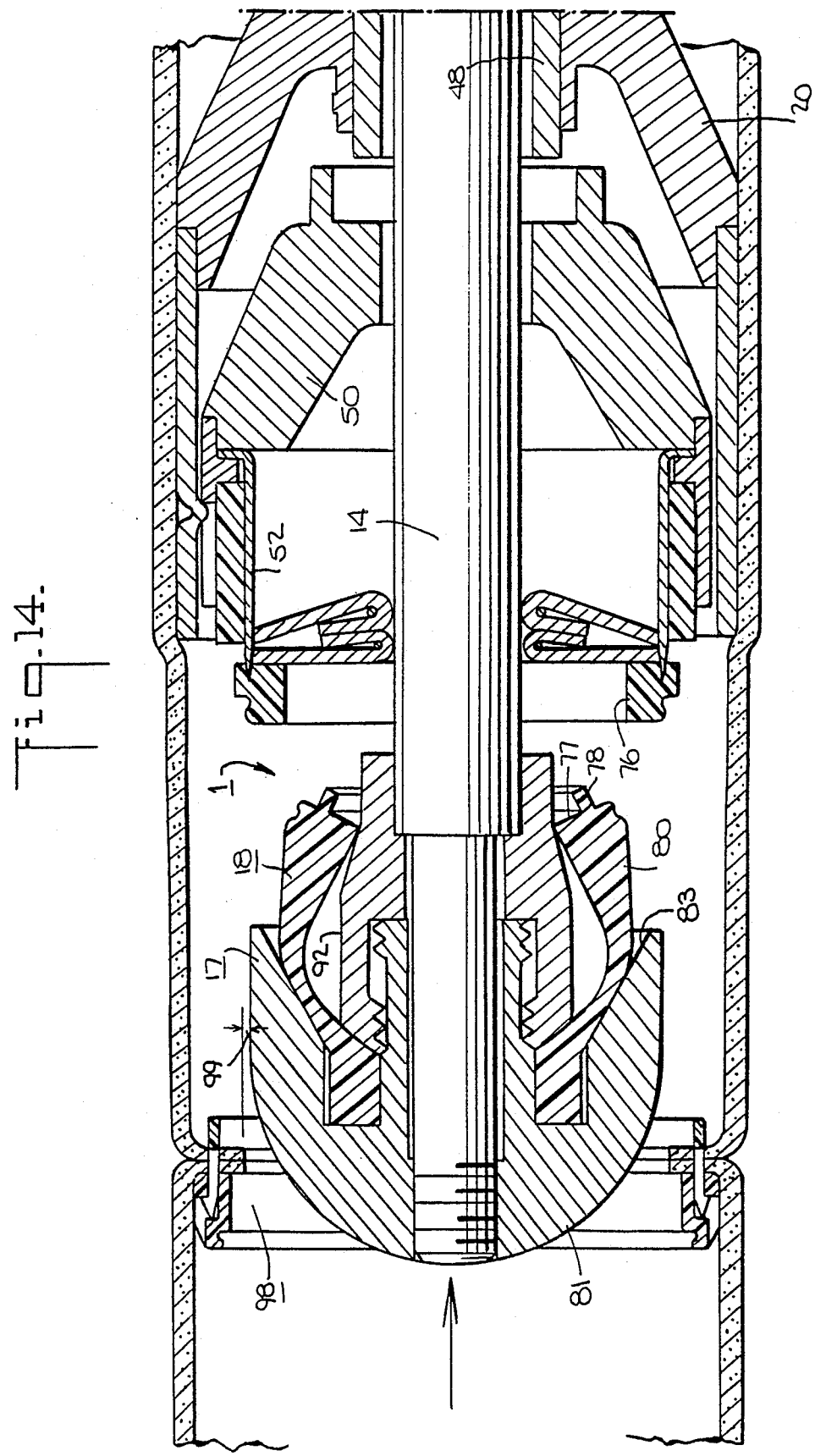
FIG. 14 illustrates a view similar to FIGS. 12 and 13 during withdrawal of the anvil assembly.

Next, the anvil assembly 17 is moved away from the holding assembly 20 by turning of the handscrew 16 (see FIG. 1). During this time, the annular cutting block 76 which has been imbedded by the annular scalpel 52 remains in place on the scalpel 52 as indicated in FIG. 14. At the same time, the annular stapling part 58 remains engaged in the retaining part 62 so as to staple the tissue ends together in a seam as indicated in FIG. 14. In addition, since the cutting block 76 has been withdrawn from the fingers 80 of the anvil 18, these fingers 80 collapse radially inwardly as also indicated in FIG. 14. The degree of collapse of the fingers 80 is such that the fingers 80 fall inside of the cutting line 99 defined by the seamed tissue. Thus, the stapling apparatus 1 may then be removed from within the stapled-together ends. Of note, when the trigger 38 (see FIG. 4) is released, the compression spring 46 biases the slider 44 to return to a proximal position which, in turn, pulls back the shaft 48 into a position as shown in FIG. 14. The actuator 50 remains within the holding assembly 20, for example, as indicated by means of a detent and a holding ring of the holding assembly 20.

The stapling part 58 and retaining part 62 can be made of any suitable materials, such as nylon, polycarbonate or other material. If a non-permanent fastener is to be used, these parts may be made of a tissue absorbable polymer.

Figure 15:
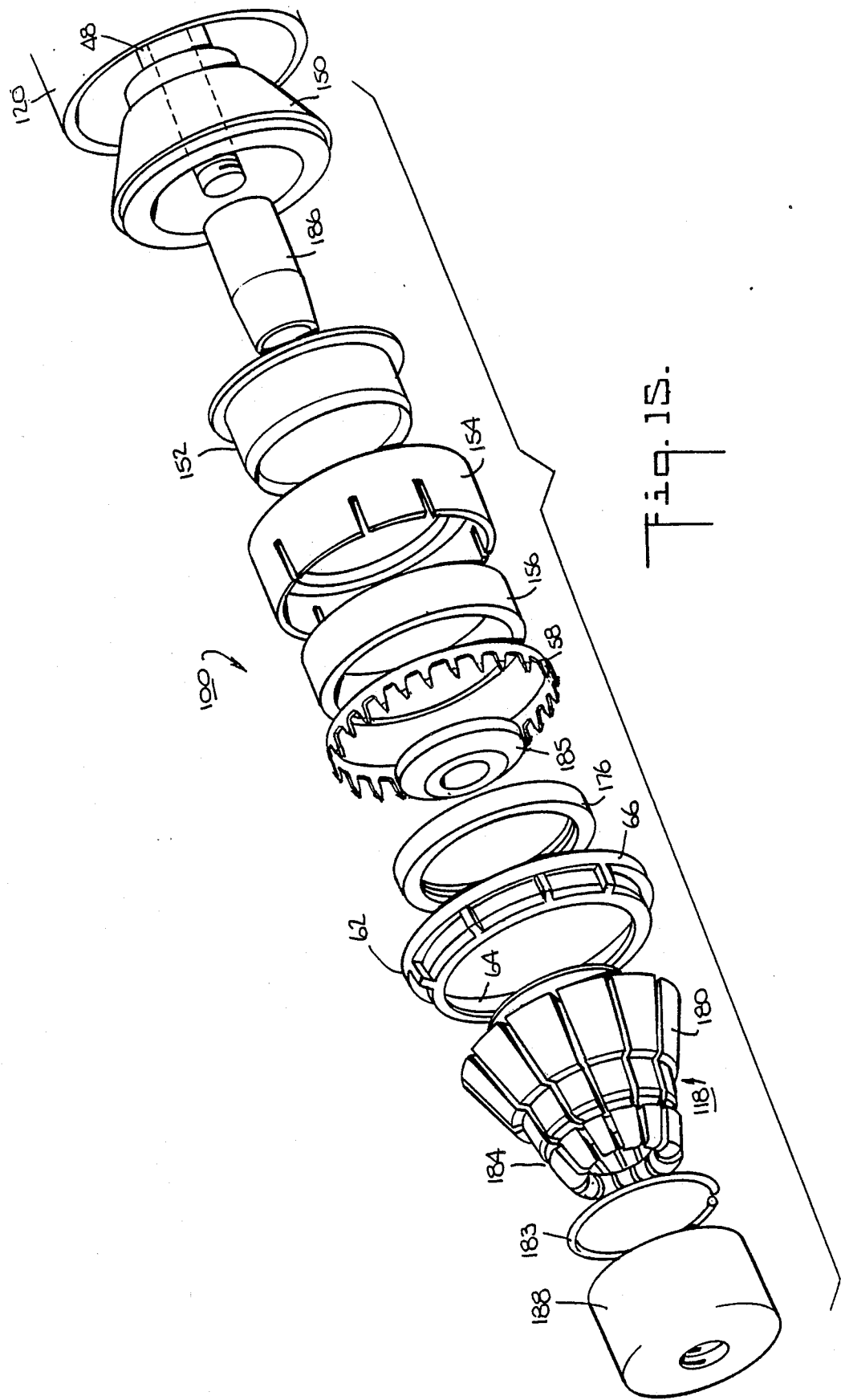
FIG. 15 illustrates an exploded view of the distal end of a surgical apparatus employing a modified anvil assembly.
Figure 16:
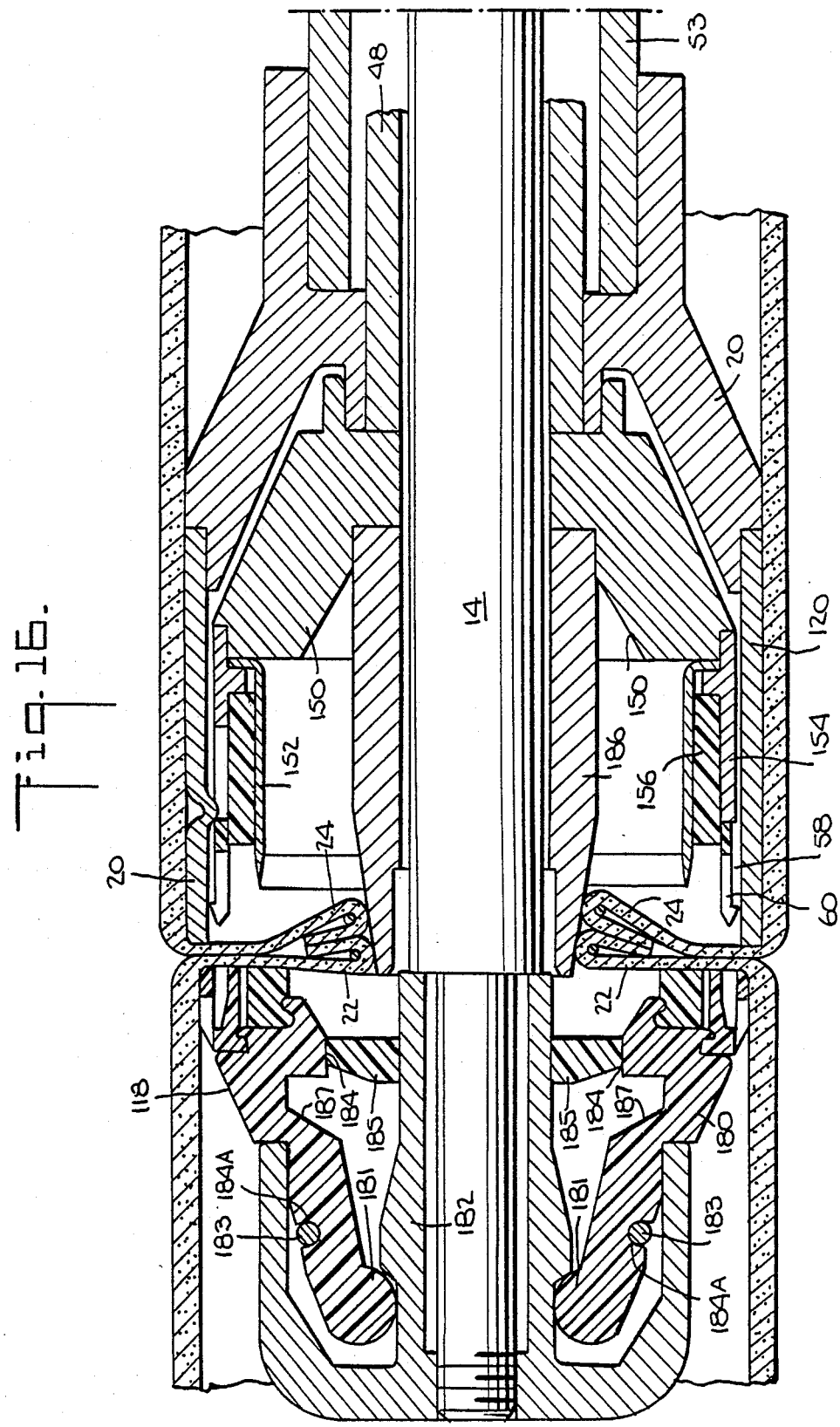
FIG. 16 illustrates a cross sectional view of the distal end of the surgical apparatus employing the anvil assembly of FIG. 15 during a stapling operation.

Referring to FIGS. 15 and 16, wherein like reference characters indicate like points as above, the stapling apparatus may be provided with a modified anvil 118 for the stapling of the surgical fastener parts 58, 62. In this respect, the anvil assembly has an anvil head 188 which is threaded onto a threaded distal end of the shaft 14 and which includes an elongated sleeve 182 with an annular recess defined by the sleeve 182 and the outer periphery of the anvil head 188. As indicated in FIG. 16, the sleeve 182 may be abutted against a shouldered portion of the shaft 14. In addition, a plurality of individual fingers 180 are circumferentially disposed with one end 181 within the recess of the anvil head 188. As shown in FIG. 16, the distal end 181 of each finger 180 rests on a sloped surface on the sleeve 182 while a proximal end rests by way of plane surfaces 184 on the outer surface of an axially movable retainer ring 185 which is mounted on the sleeve 182. In addition, a split circular spring 183 encompasses the fingers 180 and is disposed within a groove 184A in each finger so as to bias the fingers 180 onto the retainer ring 185. Each finger 180 is also provided internally with an intermediately disposed recess 187 which is spaced axially from the ring 185 and which is sized to receive the ring 185 upon axial movement of the ring 185 thereinto to permit inward radial movement of the finger 180 under the bias of the spring 183.

The fingers 180 may be made of plastic, as indicated, or may be made of anodized aluminum or other metals.

The fingers 180 of the anvil 118 are mounted within the anvil head 188 so as to be biased outwardly by the retaining ring 185 against the interior surface of the anvil head 188. The spring 183 which is in the form of a split ring serves to bias the fingers 180 against the retaining ring 185. In this respect, the fingers 180 tend to pivot about the ends 181 (see FIG. 17) within the anvil head 188.

As described above, the anvil 118 carries an annular cutting block 176 and an annular retaining part 62 of the fastener at the proximal end.

Referring to FIG. 16, the actuator of 150 in addition to carrying an annular scalpel 152 and the fastener holding assembly 20 also abuts a pusher 186 in the form of a sleeve at a distal end. As indicated, the sleeve 186 has a recessed distal end to slide over the sleeve 182 of the anvil head 188 in order to abut against the retainer ring 185 when the actuator 150 is moved distally.

Figure 17:
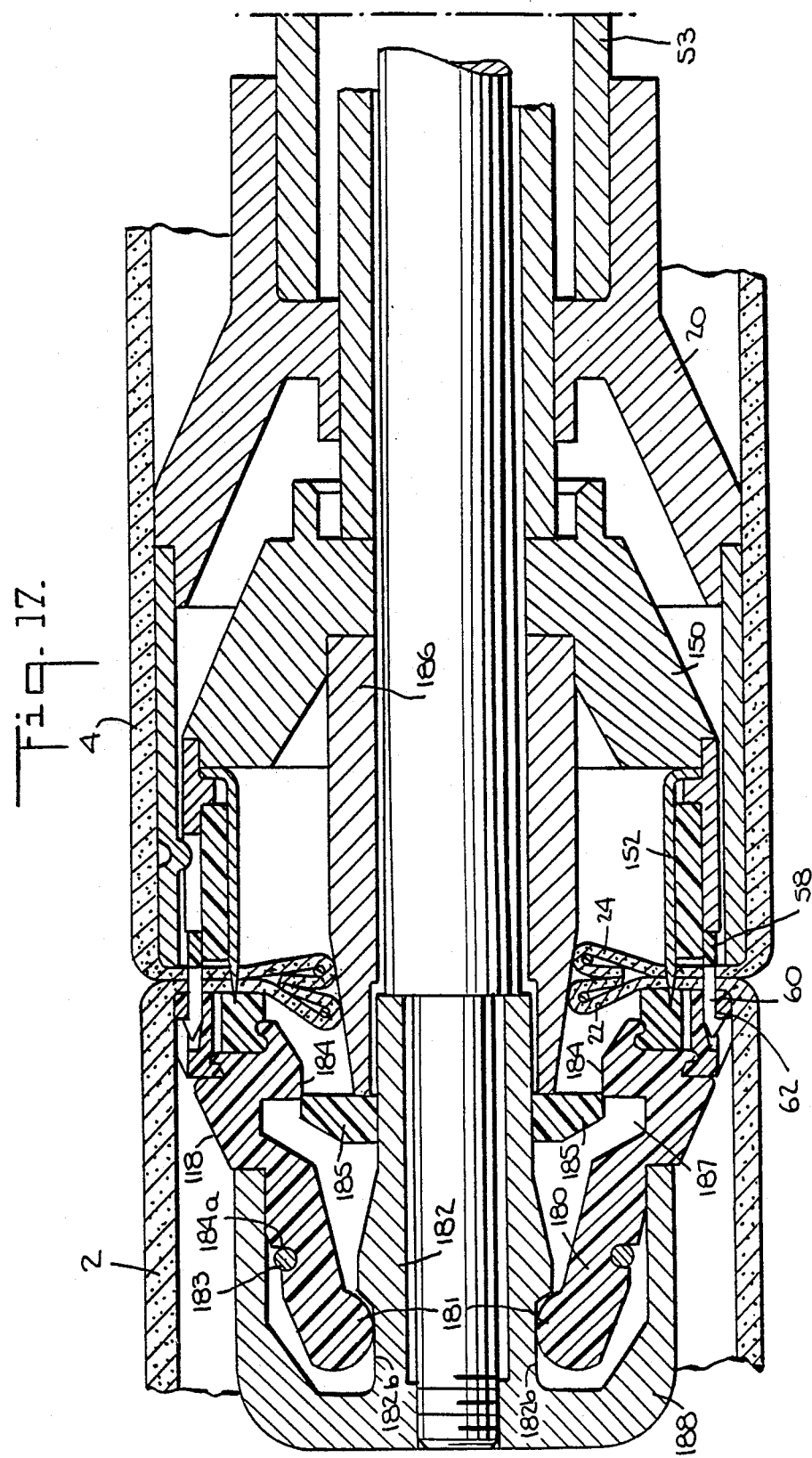
FIG. 17 illustrates a view similar to FIG. 16 of the apparatus after stapling.
Figure 18:
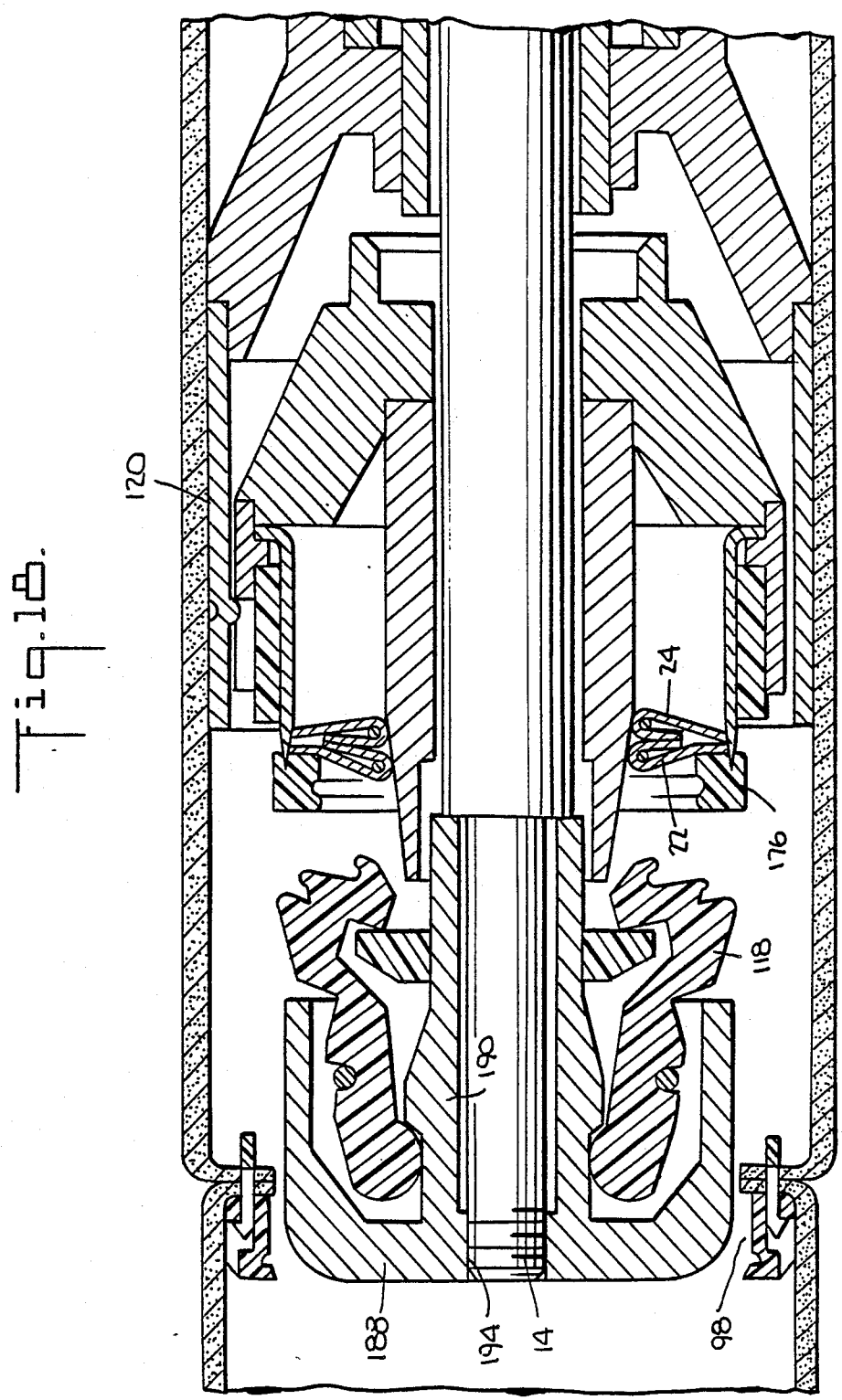
FIG. 18 illustrates a view similar to FIGS. 16 and 17 after collapsing of the anvil assembly in accordance with the invention.

Referring to FIGS. 16, 17 and 18, the operation of the stapling apparatus is similar to that as described above. In this respect, after the anvil assembly and anvil head 118 have been drawn towards the fastener holding assembly 20 to clamp the tissue areas 22, 24 therebetween, the trigger (see FIG. 1) is actuated to push the tube 48 and actuator 150 distally. At this time, the pusher 186 slides over the sleeve 182 of the anvil head 188 while the scalpel 152 severs the tissue and penetrates into the cutting block 176 and the prongs 60 of the stapling part 58 pierce the tissue and become retained in the retaining part 62 as indicated in FIG. 17. The motion of the actuator 150 is such that the pusher 186 moves the retainer ring 185 into alignment with the recess 187 of the fingers 180. Thus, the fingers 180 move under the bias of the spring 183 radially inwardly by pivoting about the ends 181.

Thereafter, the apparatus is manipulated as described above to displace the anvil 118 from the holding assembly 120 in order to insure displacement of the anvil 118 from the cutting block 176. At this time, the apparatus can be withdrawn from within the seamed tissue as indicated in FIG. 18. In this respect, the cutting block remains on the scalpel 152 while the fingers 180 are collapsed about the retaining ring 185. At the same time, the sleeve 186 has been moved proximally a slight distance away from the retaining ring 185. In this condition, the outside diameter of the fingers 180 has been reduced so as to pass through the stapled-together tissues.

Of note, the anvil head 188 is sized to be smaller than the fastener 98 and the sleeve 182 is contoured so that the anvil fingers 180 are retained in a snap fit relationship.

The invention provides a method of fastening together the ends of two tubular body organs which can be carried out in a relative minimum of time and with relatively minimal effort with respect to previously known techniques.

What is claimed is:

1. A method of stapling the tubular ends of a pair of vessels together, said method comprising the steps of clamping the tubular ends of the two vessels between an anvil assembly at a distal end of a surgical stapling apparatus and a surgical fastener holding assembly on the apparatus;

driving an annular stapling part located on one side of the clamped ends of the vessels and having prongs thereon through the clamped ends of the vessels in an annular retaining part removably supported on the anvil assembly and on an opposite side of the clamped vessels;

severing the clamped ends of the vessels on a circular cutting line disposed radially within the stapling part;

moving the anvil assembly away from the stapled ends of the vessels to withdraw the anvil assembly from the annular retaining part;

thereafter collapsing the anvil assembly radially inwardly of said retaining part and said cutting line; and then withdrawing the stapling apparatus from the stapled-together vessels.

2. A method of fastening together the ends of tubular body organs by means of an annular surgical fastener comprising the steps of positioning the annular fastener inside a first of the tubular body organs;

reducing the end of the first tubular body organ to cover the fastener;

positioning an annular anvil assembly inside a second of the tubular body organs;

reducing the annular circumference of the end of the second tubular body organ to cover an annular portion of the anvil assembly;

positioning the fastener and the anvil assembly relative to one another to clamp the reduced circumference ends of the first and second tubular body organs therebetween;

driving the fastener toward the anvil assembly and through the ends of the first and second tubular body organs to fasten the organs together;

reducing the annular circumference of the anvil assembly to a reduced circumference smaller than the inner annular circumference of the fastener; and thereafter passing the reduced circumference anvil assembly through the fastener.

3. The method as set forth in claim 2 further comprising the step of annularly cutting through the first and second tubular body organs radially inside the fastener during fastening of the organs together and before passing the reduced circumference anvil assembly through the fastener.

4. The method as set forth in claim 3 wherein the reduced circumference anvil assembly passes through the annular cut in the organs during passage through the fastener.

* * * * *

UNITED STATES PATENT AND TRADEMARK OFFICE
CERTIFICATE OF CORRECTION

PATENT NO. : 4,893,622

DATED : Jan. 16, 1990

INVENTOR(S) : DAVID T. GREEN, et al

It is certified that error appears in the above-identified patent and that said Letters Patent is hereby corrected as shown below:

Column 4, line 17 "annulgar" should be -annular-
Column 7, line 21 "in" should be -into- Signed and Sealed this Eleventh Day of June, 1991

Attest:

HARRY F. MANBECK, JR.

Attesting Officer

Commissioner of Patents and Trademarks